(12) United States Patent
Schilling et al.

(10) Patent No.: US 8,102,964 B2
(45) Date of Patent: Jan. 24, 2012

(54) BREAST LOCATING DEVICE INCLUDING AN RFID TRANSPONDER FOR A DIAGNOSTIC INSTRUMENT FOR EXAMINING A FEMALE BREAST

(75) Inventors: Harry Schilling, Eichstaett (DE); Willi Kalender, Moehrendorf (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 126 days.

(21) Appl. No.: 12/401,792

(22) Filed: Mar. 11, 2009

(65) Prior Publication Data

US 2010/0080345 A1    Apr. 1, 2010

(30) Foreign Application Priority Data

Sep. 29, 2008  (DE) .......................... 10 2008 042 430

(51) Int. Cl.
*A61B 6/04*    (2006.01)
*H05G 1/00*    (2006.01)
(52) U.S. Cl. ........... 378/37; 378/162; 378/208; 378/209
(58) Field of Classification Search .................... 378/37, 378/20, 65, 208, 209, 162; 600/407, 425
See application file for complete search history.

(56) References Cited

U.S. PATENT DOCUMENTS

| | | | |
|---|---|---|---|
| 3,673,394 A | 6/1972 | Hartmann | |
| 4,015,836 A | 4/1977 | Redington et al. | |
| 4,400,827 A | 8/1983 | Spears | |
| 4,680,028 A * | 7/1987 | Stuart | 604/74 |
| 4,709,382 A | 11/1987 | Sones | |
| 5,273,435 A | 12/1993 | Jacobson | |
| 5,308,321 A * | 5/1994 | Castro | 600/415 |
| 5,386,447 A | 1/1995 | Siczek | |
| 5,426,685 A * | 6/1995 | Pellegrino et al. | 378/87 |
| 5,528,043 A | 6/1996 | Spivey et al. | |
| 5,569,266 A | 10/1996 | Siczek | |
| 5,609,827 A | 3/1997 | Russell et al. | |

(Continued)

FOREIGN PATENT DOCUMENTS

DE    19639975    5/1998

(Continued)

OTHER PUBLICATIONS

Mun et al., "Active RFID System Augmented with 2D Barcode for Asset Management in a Hospital Setting," IEEE International Conference on RFID, Mar. 2007, pp. 205-211.

(Continued)

*Primary Examiner* — Allen C. Ho
(74) *Attorney, Agent, or Firm* — Kevin L. Daffer; Daffer McDaniel, LLP (57) ABSTRACT

A device is provided herein for locating a breast of a female patient. In one embodiment, the locating device is adapted to be inserted into an opening within a patient table. The locating device is further adapted with different sizes and shapes, and thus, can be adapted to various breast shapes. In one embodiment, the device is provided with an RFID transponder for identifying the particular locating device being used. The RFID transponder enables data about the locating device to be automatically recorded along with the image data. This enables the shape of the locating device to be taken into account when evaluating an image. Furthermore, the RFID transponder ensures that a locating device of the same shape is used for subsequent exposures of a patient's breast, so that the exposures remain comparable.

5 Claims, 6 Drawing Sheets

U.S. PATENT DOCUMENTS

| | | | |
|---|---|---|---|
| 5,664,569 A | 9/1997 | Damadian et al. | |
| 5,709,206 A | 1/1998 | Teboul | |
| 5,757,878 A | 5/1998 | Dobbs et al. | |
| 5,803,912 A | 9/1998 | Siczek et al. | |
| 6,175,117 B1* | 1/2001 | Komardin et al. | 250/363.06 |
| 6,242,743 B1 | 6/2001 | DeVito et al. | |
| 6,254,614 B1* | 7/2001 | Jesseph | 606/130 |
| 6,298,114 B1 | 10/2001 | Yoda | |
| 6,325,537 B1 | 12/2001 | Watanabe | |
| 6,358,246 B1 | 3/2002 | Behl et al. | |
| 6,415,012 B1 | 7/2002 | Taguchi et al. | |
| 6,418,188 B1 | 7/2002 | Broadnax | |
| 6,419,390 B1 | 7/2002 | Landis-Lowell | |
| 6,463,122 B1 | 10/2002 | Moore | |
| 6,480,565 B1 | 11/2002 | Ning | |
| 6,684,097 B1 | 1/2004 | Parel et al. | |
| 6,819,736 B1 | 11/2004 | Bruder et al. | |
| 6,837,772 B1* | 1/2005 | Luk | 450/51 |
| 6,872,001 B1 | 3/2005 | Gilevich | |
| 7,005,988 B2* | 2/2006 | Mathewson et al. | 340/572.4 |
| 7,065,393 B2 | 6/2006 | Sati et al. | |
| 7,149,566 B2 | 12/2006 | Lee | |
| 7,218,766 B2 | 5/2007 | Eberhard et al. | |
| 7,229,440 B2 | 6/2007 | Ho et al. | |
| 7,286,634 B2* | 10/2007 | Sommer et al. | 378/57 |
| 7,304,578 B1* | 12/2007 | Sayers et al. | 340/572.3 |
| 7,443,950 B2* | 10/2008 | Sendai | 378/37 |
| 7,453,978 B1 | 11/2008 | DiBianca et al. | |
| 7,467,892 B2 | 12/2008 | Lang et al. | |
| 7,483,511 B2* | 1/2009 | Bendahan et al. | 378/57 |
| 7,492,858 B2* | 2/2009 | Partain et al. | 378/37 |
| 7,519,209 B2 | 4/2009 | Dawant et al. | |
| 7,556,426 B2* | 7/2009 | Nakajo et al. | 378/188 |
| 7,558,370 B2* | 7/2009 | Sommer et al. | 378/57 |
| 7,573,034 B2* | 8/2009 | Heath et al. | 250/361 R |
| 7,643,670 B2 | 1/2010 | Leach et al. | |
| 7,653,229 B2 | 1/2010 | Kaufhold et al. | |
| 7,677,799 B2* | 3/2010 | Jensen et al. | 378/205 |
| 7,697,660 B2 | 4/2010 | Ning | |
| 7,743,953 B2* | 6/2010 | Okazaki et al. | 223/84 |
| 7,764,765 B2* | 7/2010 | Ohta et al. | 378/91 |
| 7,778,388 B2 | 8/2010 | Sendai | |
| 7,783,089 B2 | 8/2010 | Kaufhold et al. | |
| 7,783,094 B2 | 8/2010 | Collins et al. | |
| 7,840,046 B2 | 11/2010 | Jerebko et al. | |
| 7,850,613 B2* | 12/2010 | Stribling | 600/459 |
| 7,864,918 B2* | 1/2011 | Schilling et al. | 378/37 |
| 7,881,427 B2* | 2/2011 | Kalender et al. | 378/37 |
| 7,940,966 B2 | 5/2011 | Yu et al. | |
| 8,014,576 B2 | 9/2011 | Collins et al. | |
| 2002/0181651 A1 | 12/2002 | Shepherd et al. | |
| 2003/0072409 A1 | 4/2003 | Kaufhold et al. | |
| 2003/0204965 A1 | 11/2003 | Hennessey | |
| 2004/0066880 A1 | 4/2004 | Oikawa | |
| 2004/0082856 A1 | 4/2004 | Marmarelis | |
| 2004/0092826 A1 | 5/2004 | Corbeil et al. | |
| 2004/0238750 A1 | 12/2004 | Vafi et al. | |
| 2004/0251419 A1 | 12/2004 | Nelson et al. | |
| 2004/0254461 A1 | 12/2004 | Ackerman, III | |
| 2005/0070817 A1 | 3/2005 | Mueller, Jr. | |
| 2006/0094950 A1 | 5/2006 | Ning | |
| 2006/0145871 A1 | 7/2006 | Donati et al. | |
| 2006/0262898 A1 | 11/2006 | Partain et al. | |
| 2007/0009080 A1 | 1/2007 | Mistretta | |
| 2007/0064867 A1 | 3/2007 | Hansen et al. | |
| 2007/0092059 A1 | 4/2007 | Eberhard et al. | |
| 2007/0237306 A1 | 10/2007 | Jones et al. | |
| 2007/0238957 A1 | 10/2007 | Yared | |
| 2008/0033420 A1 | 2/2008 | Nields et al. | |
| 2008/0037703 A1 | 2/2008 | Ting | |
| 2008/0081984 A1 | 4/2008 | Lafferty | |
| 2008/0084961 A1 | 4/2008 | Keppel et al. | |
| 2008/0089471 A1 | 4/2008 | Kobayashi | |
| 2008/0101538 A1 | 5/2008 | Schliermann | |
| 2008/0187095 A1 | 8/2008 | Boone et al. | |
| 2008/0205588 A1 | 8/2008 | Kim | |
| 2008/0221443 A1 | 9/2008 | Ritchie et al. | |
| 2008/0221478 A1 | 9/2008 | Ritchie et al. | |
| 2008/0230074 A1 | 9/2008 | Zheng et al. | |
| 2009/0080604 A1 | 3/2009 | Shores et al. | |
| 2009/0196393 A1 | 8/2009 | Wang et al. | |
| 2010/0080343 A1 | 4/2010 | Kalender et al. | |
| 2010/0080344 A1 | 4/2010 | Schilling et al. | |
| 2010/0080346 A1 | 4/2010 | Kalender et al. | |
| 2010/0080347 A1 | 4/2010 | Kalender et al. | |
| 2010/0080348 A1 | 4/2010 | Kalender et al. | |
| 2010/0080349 A1 | 4/2010 | Kalender et al. | |
| 2010/0080350 A1 | 4/2010 | Kalender et al. | |
| 2010/0128843 A1 | 5/2010 | Tita | |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isotherm mapping in hyperthermia using subtraction X-ray computed tomography," Radiotherapy and Oncology, vol. 2, 1984, pp. 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Nov. 3, 2009 for U.S. Appl. No. 12/401,765.

Notice of Allowance mailed Apr. 15, 2010 for U.S. Appl. No. 12/401,765.

Office Action mailed Apr. 14, 2010 for U.S. Appl. No. 12/402,059.

Office Action mailed Apr. 1, 2010 for U.S. Appl. No. 12/402,141.

Office Action mailed Jun. 10, 2010 for U.S. Appl. No. 12/401,735.

Office Action mailed Jun. 16, 2010 for U.S. Appl. No. 12/401,906.

Office Action mailed Jul. 13, 2010 for U.S. Appl. No. 12/402,225.

Office Action mailed May 11, 2010 for U.S. Appl. No. 12/401,814.

Notice of Allowance mailed Aug. 23, 2010 for U.S. Appl. No. 12/401,765.

Notice of Allowance mailed Sep. 17, 2010 for U.S. Appl. No. 12/402,059.

Notice of Allowance mailed Sep. 29, 2010 for U.S. Appl. No. 12/401,814.

Notice of Allowance mailed Dec. 14, 2010 for U.S. Appl. No. 12/401,735.

Minhaj et al., "Laser interstitial thermotherapy (LITT) monitoring using high-resolution digital mammography: theory and experimental studies," Physics in Medicine and Biology, vol. 47, 2002, pp. 2987-2999.

Notice of Allowance mailed Mar. 8, 2011 for U.S. Appl. No. 12/402,225.

Chen et al., "Why should breast tumour detection go three dimensional?" Physics in Medicine & Biology, vol. 48, 2003, pp. 2217-2228.

Kass et al., "Snakes: Active Contour Models," International Journal of Computer Vision, 1988, pp. 321-331.

Office Action mailed Sep. 23, 2011 for U.S. Appl. No. 12/401,976.

* cited by examiner

BREAST LOCATING DEVICE INCLUDING AN RFID TRANSPONDER FOR A DIAGNOSTIC INSTRUMENT FOR EXAMINING A FEMALE BREAST

PRIORITY CLAIM

This application claims priority to pending German Application No. DE102008042430.7 filed on Sep. 29, 2008.

BACKGROUND OF THE INVENTION

1. Field of the Invention

The invention relates to a device for locating, i.e., positioning a breast of a female patient in a diagnostic instrument for breast examination. The diagnostic instrument can be an X-ray machine for imaging a female breast (mammography), a CT scanner, or an ultrasound instrument. Furthermore, the invention relates to an X-ray machine or a CT scanner with suitable means for locating or positioning a breast of a female patient, and also a method for operating a machine of this kind.

2. Description of Related Art

Various instruments, such as X-ray-machines and CT scanners, are used for examining a female breast. An embodiment of a CT scanner is disclosed, for example, in U.S. Publication No. 2006/0094950. The CT scanner described in the US Publication comprises a rotating gantry, which has an X-ray tube and an X-ray detector, disposed below a patient table on which a patient to be examined lies. A breast of the patient to be examined projects through an opening in the patient table into a beam path of the X-ray tube and detector. In order to maintain constant conditions during examination, the breast to be examined is pushed upwards by means of a pushing implement and put into a predefined shape. A displacement of the pushing implement makes it possible to adapt to different breast sizes. However, the adaptation provided by the pushing implement is only of length, and not of diameter.

Another device for stabilizing a breast of a patient is disclosed in U.S. Pat. No. 6,418,188. In this patent, a cup of rubber-like tissue is inverted to cover and draw the breast away from the patient using a cord. This elongates the breast and compresses the diameter of the breast. However, the stabilizing device described in the US patent is unable to exactly reproduce the position and shape of the breast.

Another device for stabilizing a breast of a patient is disclosed in U.S. Publication No. 2004/0082856. In this publication, outer contours of interchangeable inserts in the patient table ensure that the position of the breast is firmly fixed. Problems continue to exist in that different inserts of different sizes are used in repeated examinations, and therefore individual exposures are hardly comparable with each other.

BRIEF SUMMARY OF THE INVENTION

The following description of the objective of the disclosure provided herein and the description of various embodiments of a diagnostic instrument, a locating device, a method for applying a locating device to a breast, and a method for operating a diagnostic instrument is not to be construed in any way as limiting the subject matter of the appended claims.

According to one embodiment, a locating device is provided herein for fixing or locating a breast of a female patient within a diagnostic instrument for examining the female breast. The locating device is configured so that the breast of the patient can be fixed or located with the greatest possible comfort for the patient in a position that is reproducible over a plurality of exposures. According to another embodiment, a method is provided herein for applying a locating device to a breast of a patient.

According to one embodiment, a diagnostic instrument is provided herein for examining a female breast. The diagnostic instrument, e.g., an X-ray machine or a CT scanner, comprises a locating device for fixing or locating a breast within the diagnostic instrument. According to another embodiment, a method is providing herein for operating a diagnostic instrument of this kind.

BRIEF DESCRIPTION OF THE DRAWINGS

In the following the invention is described by way of example, without limitation of the general inventive concept, on examples of embodiments and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Figure 1:
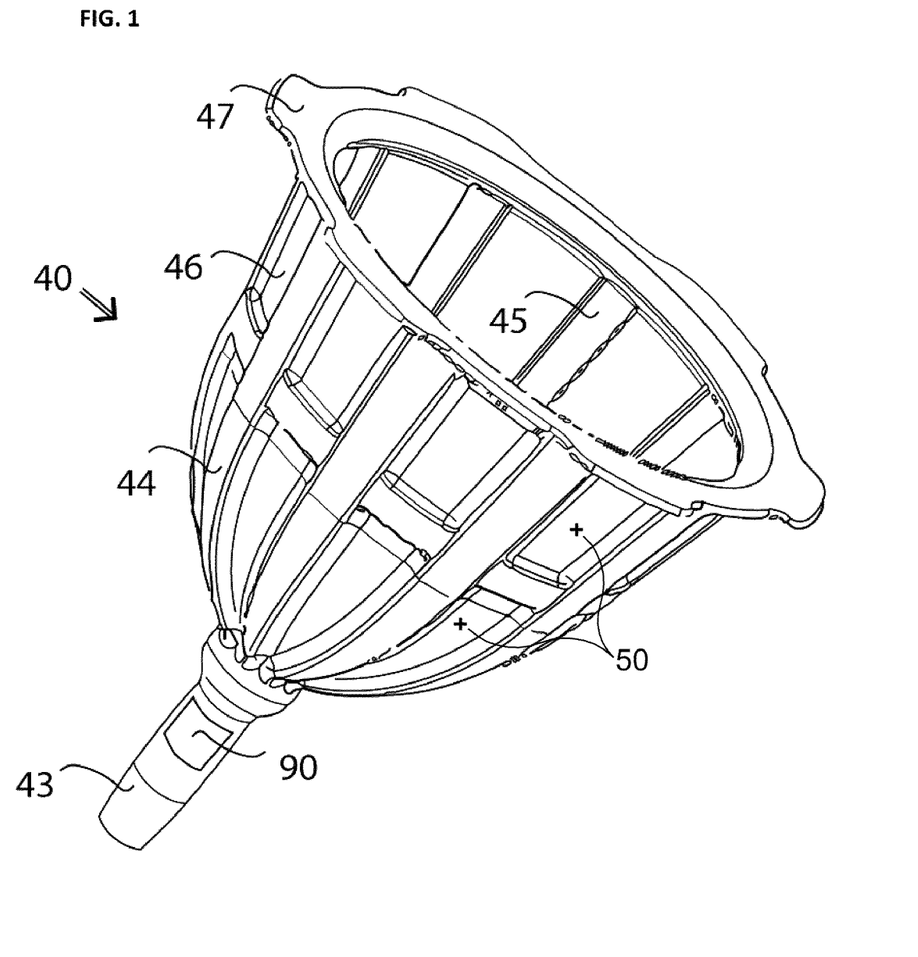
FIG. 1 shows a three-dimensional view of a device for locating a female breast.

FIG. 1 shows an embodiment of a device for locating a female breast within a diagnostic instrument. The locating device shown in FIG. 1 has a cup 40 for accommodating a breast. A basic shape of a wall 46 of the cup 40 is determined and stabilized by reinforcing ribs 44. In addition to having a shape adapted to a breast, as illustrated in FIG. 1, the cup 40 can be designed to have a cylindrical, conical, hemispheric, or any other adequate shape. In one embodiment, the wall 46 of the cup 40 is made of a material that can be punctured so that, for example, contrast agents may be injected into the breast, or tissue samples taken from the breast.

Figure 6:
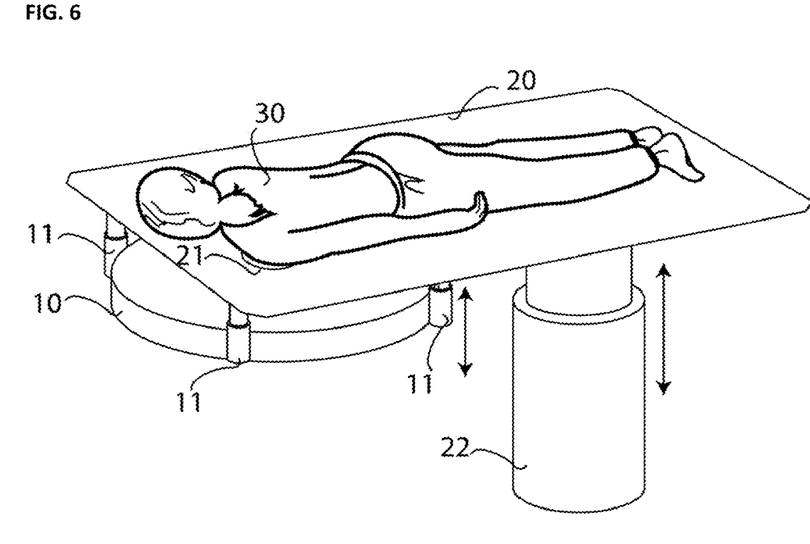
FIG. 6 shows a planar view of an X-ray machine for imaging a female breast, wherein the X-ray machine is oriented in a substantially horizontal arrangement.

At the upper end of the cup 40, corresponding to the upper end of the locating device, an opening of a sufficient size is provided for enclosing the breast. The opening is encircled by a terminating rim 47. The terminating rim 47 increases the stability of the device, and is provided with projecting portions 47a with which the rim may be fastened to a support surface (e.g., patient table 20, as shown in FIG. 6) of the diagnostic instrument. Cups 40 of various sizes and shapes are provided to accommodate different breast sizes of patients.

Figure 7:
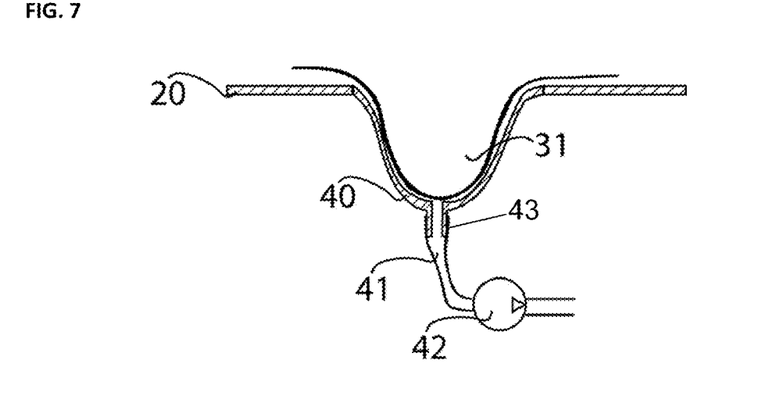
FIG. 7 shows a device for locating a breast, the device being incorporated in a patient table of an X-ray machine.

In one embodiment, the locating device includes a vacuum system for shaping a breast, so that the breast conforms exactly to the shape of the cup 40. An embodiment of a vacuum system connected to the locating device via a tubing connector 43 is shown in FIG. 7. Referring to FIGS. 1 and 7, air is drawn off from an inner space of the cup 40 through at least one suction channel 45 incorporated, e.g., within a reinforcing rib 44. Drawing air off from the inner space holds the locating device firmly against the breast and causes the breast to exactly conform to the shape of the cup of the locating device. In some embodiments, a plurality of suction channels and corresponding openings may be provided to increase suction.

In one embodiment, an RFID transponder 90 is provided for identifying the cup 40. The RFID transponder 90 may store technical information directly on the locating device, such as shape, size, material, sterility, X-ray properties, date of manufacture, period of use, number of applications or performed examinations, serial number, suitability for use in a particular X-ray machine etc. The data may be programmed in the transponder during manufacture or during use.

Figure 2:
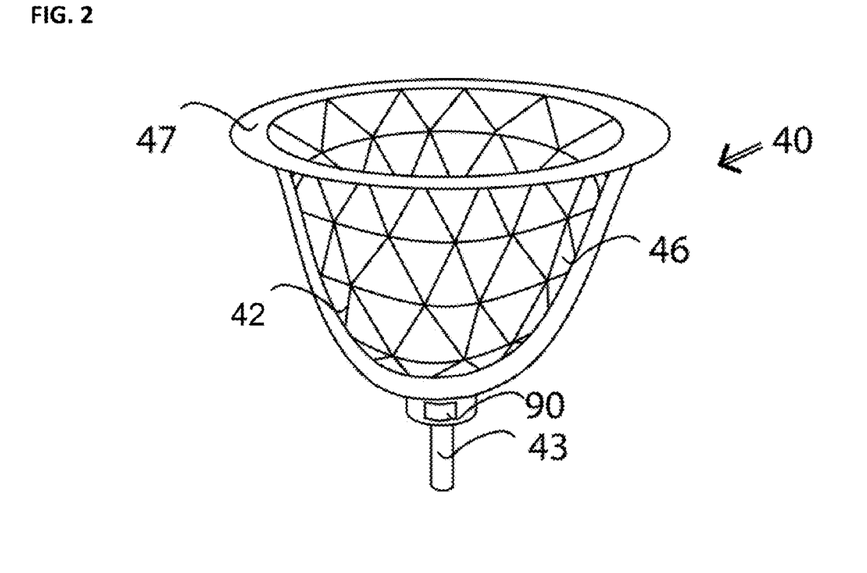
FIG. 2 shows a three-dimensional view of another device for locating a female breast.

FIG. 2 shows another embodiment of a breast-locating device. In this embodiment, the wall 46 of the cup 40 comprises a lattice of woven fabric 42, instead of reinforcing ribs 44. In general, the lattice of woven fabric 42 may be formed so that it draws together and compresses a breast when tension is applied, e.g., to the sides of the tubing connector 43. Since air enters through the mesh, it is not possible to create a sub-pressure system by connecting a vacuum system to the tubing connector 43 of the woven fabric breast locating device. However, if the device is provided on the inside with an elastic foil or coating, the woven fabric breast locating device can be rendered airtight thereby, so that air can be sucked out of the intermediate space between the wall 46 and the breast.

Figure 3:
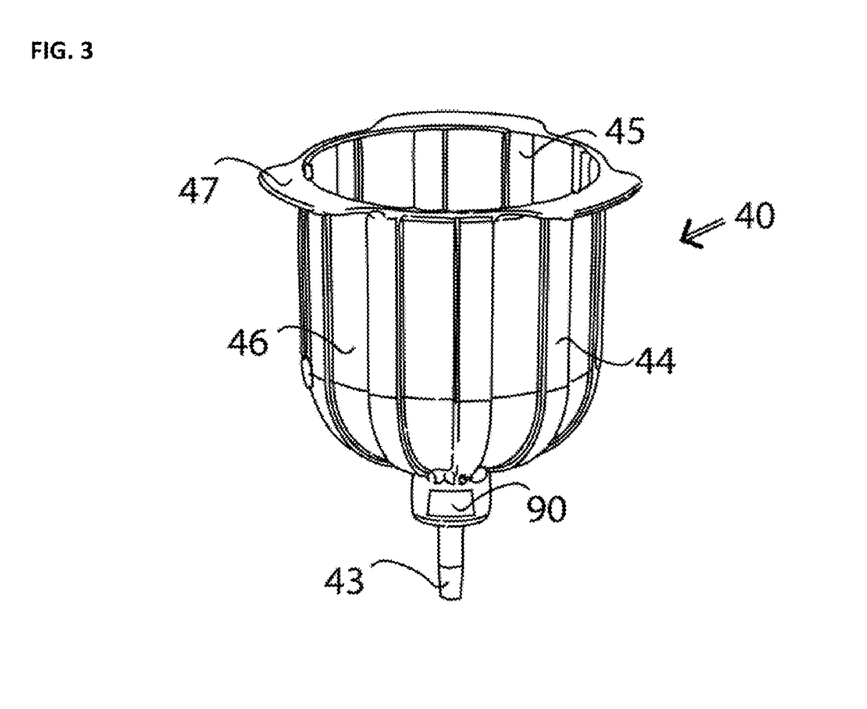
FIG. 3 shows a three-dimensional view of another device for locating a female breast.

FIG. 3 shows another embodiment of a breast locating device. In this embodiment, the cup of the locating device 40 comprises an approximately cylindrical basic shape. The remaining features correspond to those shown in FIG. 1 and described above.

Figure 4:
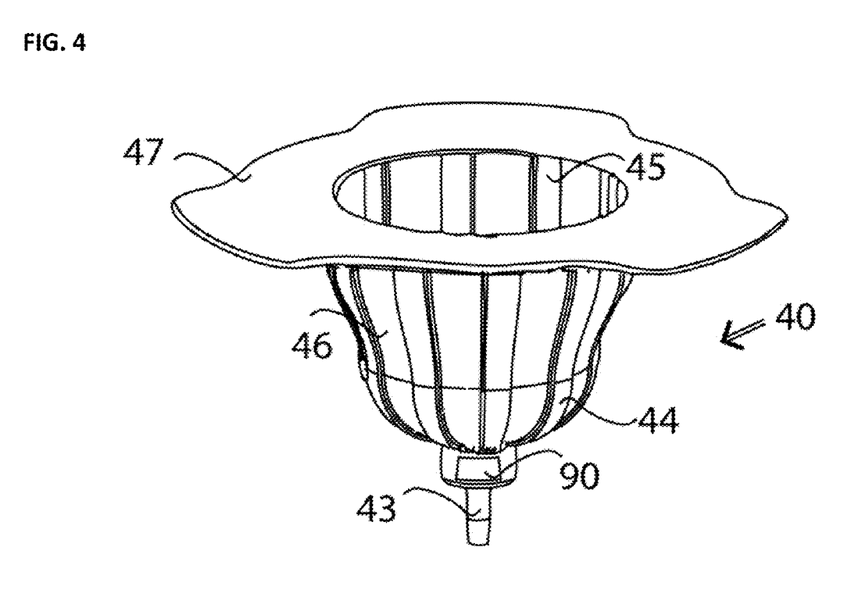
FIG. 4 shows a three-dimensional view of another device for locating a female breast.

FIG. 4 illustrates a breast locating device similar to that shown in FIG. 3. However, device shown in FIG. 4 is designed for smaller breasts having a smaller cup size. It may be used as an alternative to the device shown in FIG. 3.

Figure 5:
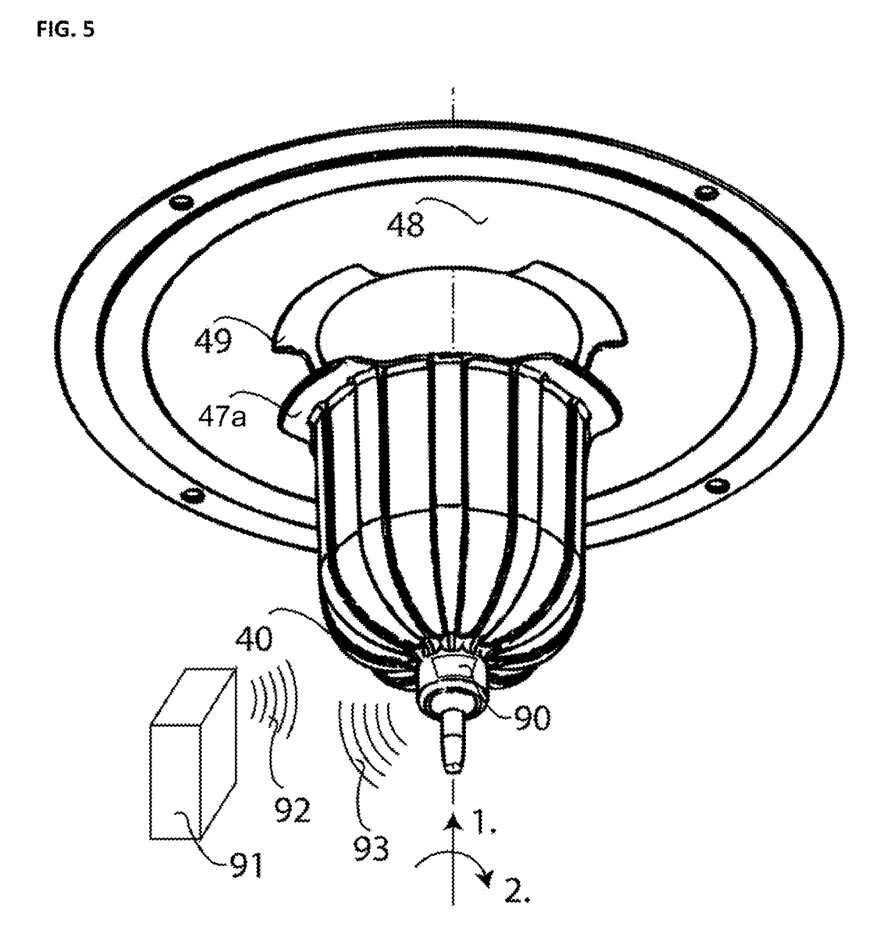
FIG. 5 shows an incorporation of a breast locating device within a patient table of an X-ray machine.

FIG. 5 shows an embodiment of a breast locating device incorporated within a support surface 20 of a diagnostic instrument. The support surface comprises an accommodating ring 48, which may be used for rough adaptation to different breast sizes. In the embodiment of FIG. 5, the locating device is fastened to the accommodating ring 48 by means of projecting portions 47a of the terminating rim 47. To fasten the locating device within the ring 48, the locating device is first slid upwards into the guide groove 49 (1.) and then rotated (2.). This principle corresponds to that of a quarter-turn fastener. However, other fastening mechanisms, such as a magnetic fastener, a snap fastener, or even a Velcro fastener may be used to fasten the locating device within the ring 48.

One advantage provided herein is that the locating device can be easily exchanged (e.g., for locating device having a smaller or larger cup size, a different shape and/or a different material). As shown in FIG. 5, the locating device may be applied from below, i.e., from the side of the support surface facing away from the patient. This enables vacuum tubing to be connected to the locating device. In another embodiment, the locating device may be inserted through the support surface from the patient's side (i.e., from above). This embodiment would allow the side of the support surface facing away from the patient to be completely incorporated within an enclosed housing. If an enclosed housing is used, a plug-in system may be provided on the housing for the vacuum system. A plug-in system of this kind can be achieved with magnetic coupling.

FIG. 5 also schematically illustrates communication between an RFID transponder 90 and an RFID reader 91. The RFID reader 91 sends a query signal 92 which is answered by the RFID transponder 90 in the form of an acknowledge signal 93. RFID (Radio Frequency Identification) is generally understood to mean an identification by radio signals or other electromagnetic signals. In one embodiment, a passive transponder which receives its energy from the reader is used for reasons of cost. Especially preferred is an RFID system according to one of the following standards: ISO/IEC 10536, ISO/IEC 14443, ISO/IEC 15693, ISO 69873.

FIG. 6 shows an embodiment of an X-ray machine for imaging a breast of a female patient. A patient 30 lies on a patient table 20. A breast to be examined is suspended via a breast cut-out portion 21 of the patient table 20 into an imaging range of a gantry 10 and is held there by a breast locating or fixing means. The breast locating means is not discernible in the perspective view of FIG. 6, because it is covered by the patient's body. Embodiments of the breast locating means are shown, however, in FIGS. 1-5 and described above.

In the embodiment of FIG. 6, gantry 10 is a spiral computer tomograph gantry with an X-ray tube and a detector which rotate around a breast to be examined. The breast is imaged during the rotation. Simultaneously with the rotation, a shift or displacement of the gantry along a vertical direction is performed via a gantry lift drive 11, so that the breast is scanned along a spiral-shaped track. The height of the patient table 20 is adjustable via a patient table lift drive 22. In one embodiment, a firmly installed patient's table may be additionally rotatable about the axis of the patient table lift drive 22.

FIG. 7 is a cross-sectional view illustrating an example of a locating device in which the cup 40 is inserted into the opening 21 of the support surface 20. In one example, the cup 40 is connected to the support surface via a flat conical fit. As shown in FIG. 7 and indicated above, a vacuum pump 42 is connected via tubing 41, so that the breast 31 of the patient is fixed in the locating device by sub-pressure.

Figure 8:
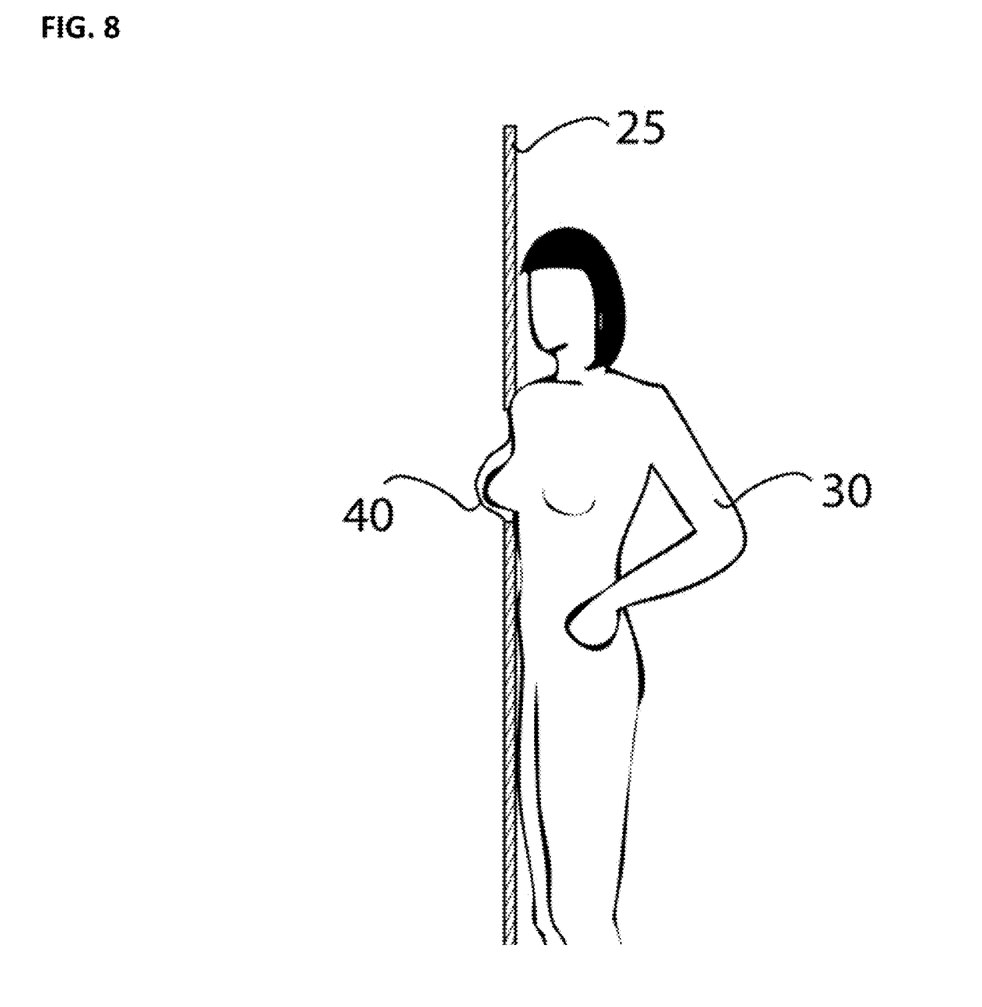
FIG. 8 shows a cross-sectional view of an X-ray machine in a vertical, rather than horizontal arrangement.

FIG. 8 shows another embodiment of an X-ray machine for imaging a breast of a female patient. Instead of lying on a table 20, as shown in FIG. 6, the patient presses her body against a surface 25 of a substantially vertically disposed X-ray machine. In this embodiment, the cup 40 is inserted within an opening of the substantially vertical support surface 25.

As noted above, a device is provided herein for locating or fixing a breast of a female patient within a diagnostic instrument. In general, the breast locating device described herein comprises a cup 40, which can be inserted within an opening in a support surface (which may be a patient table or a substantially vertical surface). For identifying the locating device, the locating device is provided with an RFID transponder 90.

It is especially advantageous for various locating devices to be designed to have different sizes and/or different shapes adapted to fit various breast shapes. Thus, in each case, a suitable locating device can be selected to fit the shape of a particular breast. The incorporation of an RFID transponder 90 ensures that a locating device of the same shape and size is always used in repeat examinations of the same patient.

As noted above, the RFID transponder 90 may store technical information, such as shape, size, material, sterility, X-ray properties, date of manufacture, period of use, number of applications or performed examinations, serial number, suitability for use in a particular X-ray machine etc. In one embodiment, the RFID transponder enables the shape of the locating device to be taken into account automatically during an evaluation of image data. Thus, collimation or measurement field can be optimally set on the basis of data from the RFID transponder in order to minimize radiation load and optimize image quality. Other parameters for methods of correction can be similarly set. For example, a serial number or another identification of the locating device can be automatically read out and recorded along with the image data. Other identification systems, such as control cams or barcodes, can be provided along with or alternative to the RFID transponder 90. In one embodiment, sensors for detecting biological, chemical or physical parameters such as temperature, pressure etc. can be provided on the locating device. Signals from these sensors can be transmitted by radio or via the RFID transponder 90.

In one embodiment, reinforcement ribs 44 are provided for determining the contour of a wall 46 of the cup 40 and for simultaneously stabilizing it. The wall itself is preferably made of a material that can be punctured, so that, for example, contrast agents may be injected into a breast or tissue samples taken from it.

In another embodiment, the cup 40 may comprise an optically transparent material or at least have transparent regions. In addition or alternatively, identification marks 50 may be provided on the cup 40. Marks of this kind may indicate, for example, puncturing positions for biopsy needles with which definite positions inside a breast may be reached. In addition, holes or openings for medical instruments can be provided in the cup 40.

In one embodiment, a vacuum system is provided for conforming a breast to the shape of the locating device. In some embodiments, the locating device may be held to the breast by the sub-pressure created by the vacuum system. A tubing connection 43 or another means (such as, for example, a plug-in connector) is provided on the locating device for connecting a vacuum pump 42 to the device via a tubing 41. When air is extracted from the inner space of the locating device (e.g., by means of suction channels 45), the breast conforms exactly to the shape of the locating device, and the locating device is held firmly against the breast. In one embodiment, the locating device may be provided with a multitude of suction channels 45 and air exit openings through which air can pass from the inside of the locating device into the suction channels.

According to one embodiment, a set of locating devices comprises a plurality of the above illustrated locating devices of different sizes or cups of different sizes. In one embodiment, a plurality of cups having diameters in a range from about 80 mm to about 180 mm is provided. In one embodiment, information concerning the available cup sizes is stored in the RFID transponder of each locating device. This information may consist of a direct statement of size, such as cup diameter or length. However, the statements may also be indirect (such as, e.g., a serial number). If indirect statements are stored in a database, a reading instrument can be used along with the RFID transponder to draw conclusions concerning, e.g., the size of the cup.

According to another embodiment, an X-ray machine, in particular a CT scanner, is provided with a device for locating a breast, as illustrated above. In one embodiment, the X-ray machine is also provided with a reading instrument for an RFID transponder (located, e.g., on the breast locating device). In such an embodiment, the X-ray machine may have a data base of scan parameters (such as, e.g., voltage, current, aperture, spiral length, water correction parameter, scattered radiation correction parameter, ring artifact correction parameter) for different breast locating devices, or at least a data connection to a data base of this kind. Such a data base may also contain the RFID transponder identifications corresponding to the stored scan parameters.

In some embodiments, it may be possible to position a patient on the support surface 20 of the X-ray machine with the cup 40 already inserted within the support surface. However, it is sometimes easier to apply the cup to the patient before the patient is positioned on the support surface 20. The breast locating device described herein enables the cup to be applied to the patient before the patient is positioned on the support surface 20.

According to one embodiment, a method for applying a locating device to a breast of a patient comprises applying the cup to the breast and activating a vacuum system comprising a vacuum pump and tubing. As best shown in FIGS. 6-7, the vacuum tubing is inserted through the breast cutout portion 21 of the support surface 20 and connected to the breast locating device at the tube connector 43. Once the vacuum system is activated (i.e., to hold the locating device in place and conform the breast to the cup), the patient is positioned on the support surface 20.

According to an alternative embodiment, a method for applying a locating device to a breast of a patient comprises holding the cup to the breast, and placing the patient on the support surface 20. In this embodiment, a holder for the cup is provided on the support surface, with the holder locking automatically, for example, with a magnetic lock. In this embodiment, it is preferred that the vacuum connection be produced automatically, for example, with a magnetic clutch. For this to occur, the cup is connected to the vacuum pump.

According to one embodiment, a method for using an X-ray machine comprises: (a) inserting a locating device into a support surface; (b) reading out data from an RFID transponder coupled to the locating device; (c) checking whether the locating device has already been used from data read out of the RFID transponder; (d) issuing an error report if the locating device has already been used (optionally, the method can be ended at this step); (e) if an error report has been issued, writing data into the RFID transponder to indicate that the locating device has already been used (optionally, the number of previous uses can be written into the RFID transponder, or the count of a corresponding counter in the RFID transponder can be increased); (f) automatically selecting at least one optimal scan parameter from a plurality of scan parameters comprising voltage, current, aperture, spiral length, water correction parameter, scattered radiation correction parameter, and ring artifact correction parameter on the basis of data read out from the RFID transponder; and (g) performing a scan, i.e., an X-ray imaging.

For selecting the at least one optimal scan parameter in step (f), preferably a data base or at least a table with suitable scan parameters for various RFID transponder identifications is stored in, or available to, the X-ray machine.

It will be appreciated to those skilled in the art having the benefit of this disclosure that this disclosure is believed to provide a device for locating a breast within an X-ray machines for imaging a breast. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine for imaging a breast of a female patient, comprising:
    an X-ray tube and an X-ray detector;
    a support surface for accommodating a patient, wherein the support surface comprises a cutout portion for the patient's breast;
    at least one device for locating the patient's breast within the cutout portion, wherein the at least one device comprises:
        a cup for accommodating a breast, wherein the cup is inserted through or attached to the cutout portion; and
        an RFID transponder located on the cup for storing and communicating information about the cup; and
    an RFID reader for communicating with the RFID transponder of the at least one device, wherein said communication includes at least one of querying data from the RFID transponder and storing data in the RFID transponder.

2. The X-ray machine according to claim 1, wherein the X-ray machine comprises a data base of scan parameters for various devices for locating a breast, or at least a data connection to such a data base.

3. The X-ray machine according to claim 1, wherein the X-ray machine is a computer tomography (CT) scanner.

4. A method for operating an X-ray machine adapted for imaging a breast of a patient, comprising:
    inserting a device for locating the breast of the patient into a support surface of the X-ray machine;
    positioning the patient on the support surface such that the breast is accommodated in the device;
    reading data communicated from an RFID transponder located on the locating device;
    using the data read out of the RFID transponder to determine whether the locating device has been previously used;
    issuing an error report if the locating device has been previously used;
    writing data into the RFID transponder to indicate that the locating device has been previously used;
    automatically selecting at least one optimal scan parameter on the basis of data read out from the RFID transponder; and
    performing a scan of the patient's breast using the X-ray machine.

5. The method according to claim 4, wherein the at least one optimal scan parameter is selected from a group consisting of voltage, current, aperture and spiral length, as well as water correction, scattered radiation correction, and ring artifact correction parameters.

* * * * *